US011785856B2

United States Patent
Chen et al.

(10) Patent No.: US 11,785,856 B2
(45) Date of Patent: Oct. 10, 2023

(54) METHOD AND APPARATUS FOR ENERGY HARVESTING USING POLYMERIC PIEZOELECTRIC STRUCTURES

(71) Applicant: THE TRUSTEES OF DARTMOUTH COLLEGE, Hanover, NH (US)

(72) Inventors: Zi Chen, Hanover, NH (US); John X. J. Zhang, Hanover, NH (US); Lin Dong, Hanover, NH (US); Zhe Xu, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 787 days.

(21) Appl. No.: 16/481,023

(22) PCT Filed: Jan. 26, 2018

(86) PCT No.: PCT/US2018/015419
§ 371 (c)(1),
(2) Date: Jul. 25, 2019

(87) PCT Pub. No.: WO2018/140709
PCT Pub. Date: Aug. 2, 2018

(65) Prior Publication Data
US 2019/0393406 A1 Dec. 26, 2019

Related U.S. Application Data

(60) Provisional application No. 62/450,948, filed on Jan. 26, 2017.

(51) Int. Cl.
*H10N 30/30* (2023.01)
*A61N 1/378* (2006.01)
(Continued)

(52) U.S. Cl.
CPC ......... *H10N 30/306* (2023.02); *A61N 1/3785* (2013.01); *H02N 2/186* (2013.01); *H10N 30/857* (2023.02)

(58) Field of Classification Search
CPC .... H01L 41/193; H01L 41/1136; H02N 2/186
See application file for complete search history.

(56) References Cited

U.S. PATENT DOCUMENTS 6,424,079 B1 * 7/2002 Carroll ................... H02N 2/185
310/339
6,545,384 B1 * 4/2003 Pelrine ................... H01L 41/094
977/788

(Continued)

FOREIGN PATENT DOCUMENTS

| CN | 103550864 | 7/2015 | |
|---|---|---|---|
| CN | 105305881 | 2/2016 | |
| EP | 2439000 A1 * | 4/2012 | ............... B06B 1/06 |

OTHER PUBLICATIONS

International Patent Application No. PCT/US18/15419; International Search Report and Written Opinion dated Apr. 13, 2018; 8 pgs.

*Primary Examiner* — J. San Martin
(74) *Attorney, Agent, or Firm* — Cozen O'Connor

(57) ABSTRACT

A piezoelectric energy harvester has a layered structure comprising a first electrode, a polymeric piezoelectric material, and a second electrode, the layered structure coupled to receive mechanical stress from the environment, and the first and second electrode electrically coupled to a power converter. The power converter is adapted to charge an energy storage device selected from a capacitor and a battery. The method of harvesting energy from the environment includes providing a piezoelectric device comprising a layer of a polymeric piezoelectric material disposed between a first and a second electrode; coupling mechanical stress derived (Continued)

from an environment to the piezoelectric device; and coupling electrical energy from the piezoelectric device.

15 Claims, 7 Drawing Sheets

(51) Int. Cl.
  *H02N 2/18* (2006.01)
  *H10N 30/857* (2023.01)

(56) References Cited

U.S. PATENT DOCUMENTS

| | | | |
|---|---|---|---|
| 8,134,282 B1* | 3/2012 | Churchill | H02N 2/181 |
| | | | 310/329 |
| 8,319,402 B1 | 11/2012 | Churchill et al. | |
| 10,137,306 B2* | 11/2018 | Dagdeviren | H02N 2/181 |
| 2001/0035723 A1* | 11/2001 | Pelrine | H01L 41/193 |
| | | | 318/116 |
| 2010/0171393 A1* | 7/2010 | Pei | H01L 41/098 |
| | | | 359/566 |
| 2011/0309716 A1* | 12/2011 | Jenninger | B32B 27/325 |
| | | | 156/92 |
| 2015/0084480 A1* | 3/2015 | Savelli | H02N 10/00 |
| | | | 290/1 R |
| 2015/0188030 A1 | 7/2015 | Andosca et al. | |
| 2015/0318462 A1* | 11/2015 | Kim | H01L 41/0933 |
| | | | 310/332 |
| 2016/0156287 A1* | 6/2016 | Yang | H10N 30/306 |
| | | | 310/339 |
| 2016/0346556 A1* | 12/2016 | Slepian | H02N 2/181 |
| 2017/0324022 A1* | 11/2017 | Ting | H10N 30/88 |
| 2021/0273588 A1* | 9/2021 | Chang | H10N 30/857 |
| 2021/0370053 A1* | 12/2021 | Jin | A61N 1/36071 |

\* cited by examiner

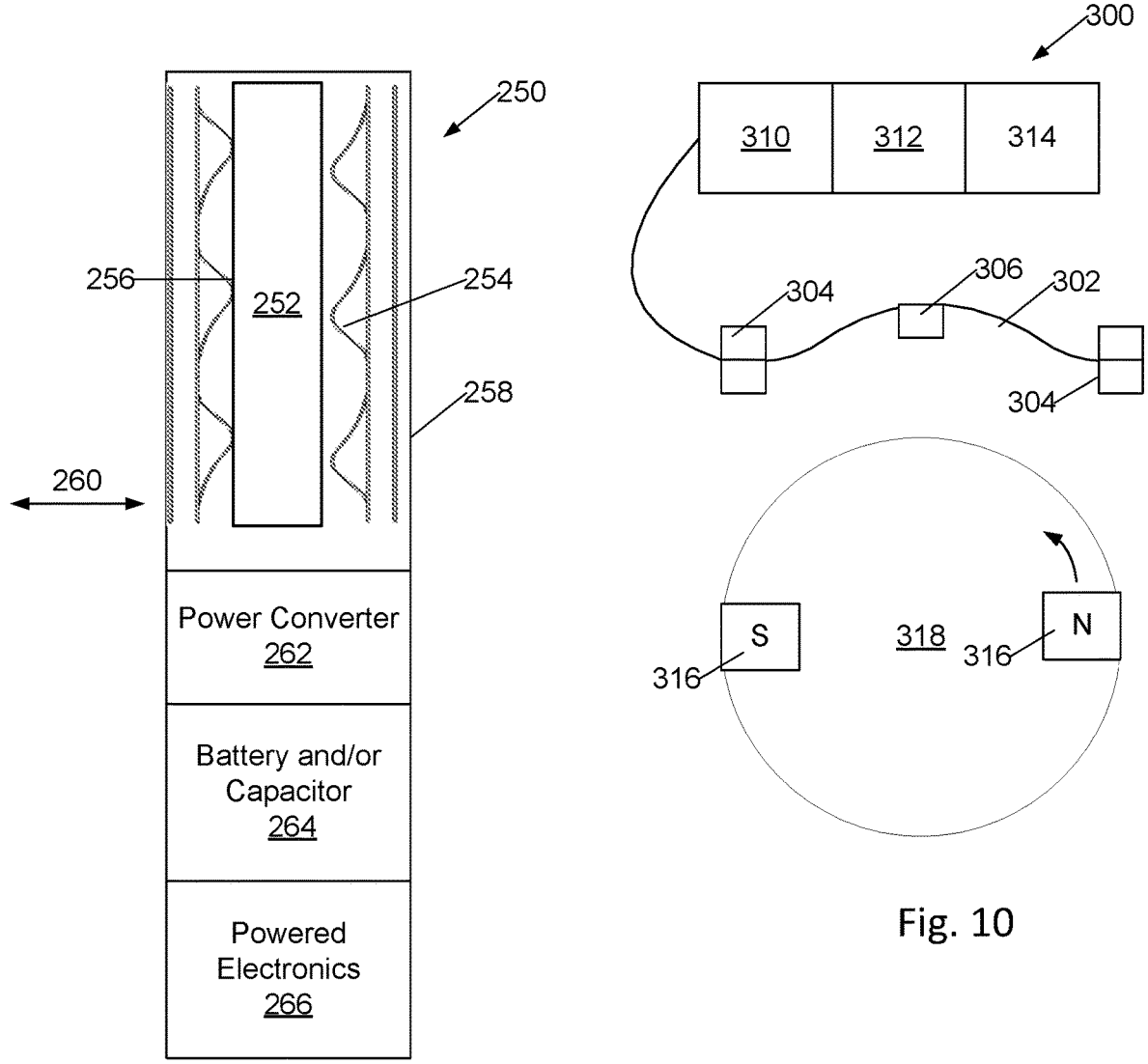

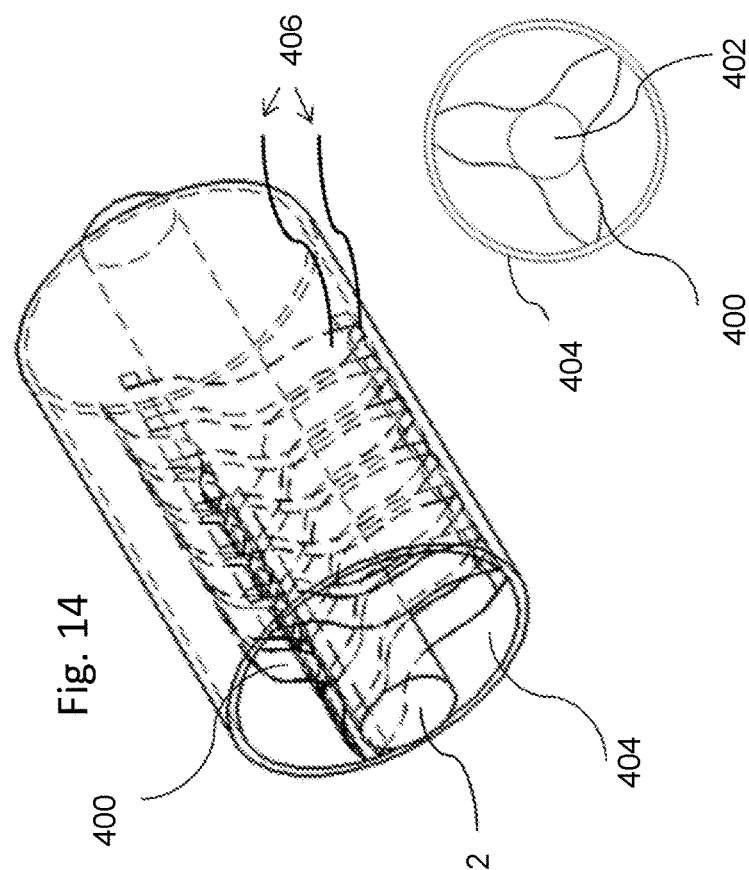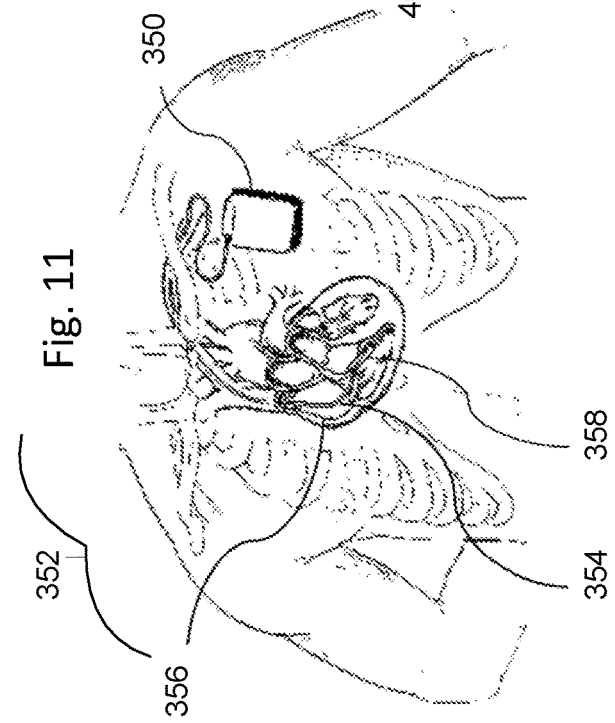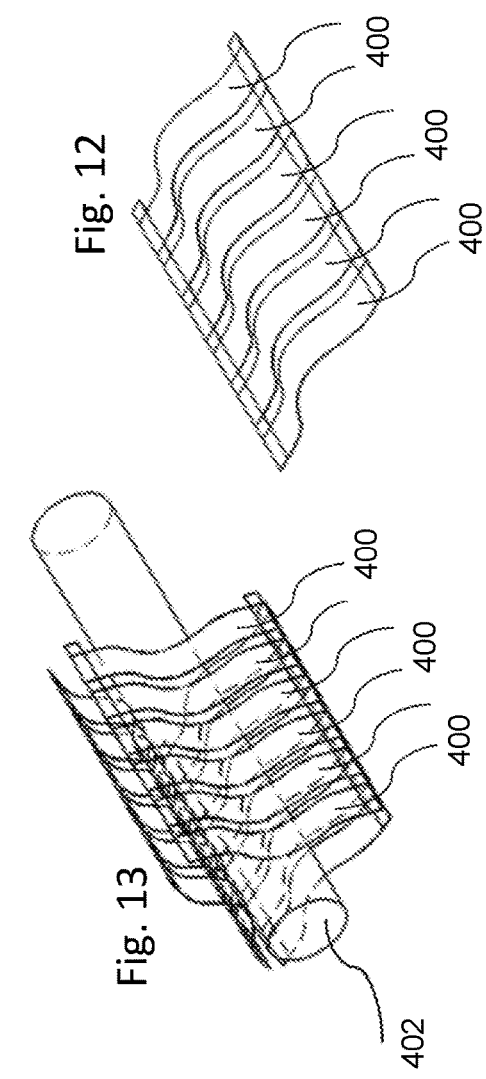

METHOD AND APPARATUS FOR ENERGY HARVESTING USING POLYMERIC PIEZOELECTRIC STRUCTURES

CROSS-REFERENCE TO RELATED APPLICATIONS

The present application is a 35 U.S.C. § 371 filing of International Application No. PCT/US2018/015419, filed Jan. 26, 2018, which claims priority to U.S. Provisional Patent Application No. 62/450,948 filed Jan. 26, 2017, the entire contents of which are incorporated herein by reference.

GOVERNMENT RIGHTS

This invention was made with government support under grant number R01 HL137157 awarded by the National Institutes of Health. The government has certain rights in the invention.

BACKGROUND

Many electrically-powered implantable devices, from cardiac pacemakers through deep-brain neurostimulators and hearing prosthetics like cochlear implants, are used in humans. Many other devices, such as optical cortex stimulators for visual prosthetics, are in development and may soon be approved for wider use. These devices typically require a source of electricity, such as a battery. When batteries fail or wear out, these implantable devices may require surgery to replace either the battery or the device with battery.

Wires and similar objects that pass through the skin to recharge batteries or power devices may lead to infection and are therefore rarely used to power implantable devices. While some devices have used transdermal electromagnetic induction coil chargers to pass electrical energy through the skin, transdermal charging requires people maintain and regularly use a mating, external, charging device.

Solar panels, a common device for harvesting energy from the environment, are not often implanted to power or recharge implantable devices in part because skin absorbs light.

In nonmedical fields, there are many devices that require small amounts of power where it is inconvenient to provide grid-power connection—especially in retrofit situations or where movement is likely to damage power connections. While solar panels are often used to harvest energy to power these devices, solar panels are useful only where significant light is available.

Where devices are subjected to frequent movement, like wristwatches or add-on sensors for reciprocating machinery, energy has been harvested through movable weights within the device like mechanical self-winding watches. Some other devices have harvested energy from movement by providing a weighted magnet that moves relative to a coil of the device as in shaker-type rechargeable flashlights.

Piezoelectric materials are materials that, when subjected to mechanical stress, generate electricity, or bend, twist, or otherwise deform in response to a voltage applied to them.

SUMMARY

In an embodiment, a piezoelectric energy harvester has a layered structure comprising a first electrode, a polymeric piezoelectric material, and a second electrode, the layered structure coupled to receive mechanical stress from the environment, and the first and second electrode electrically coupled to a power converter. The power converter is adapted to charge an energy storage device selected from a capacitor and a battery.

In another embodiment, a method of harvesting energy from the environment includes providing a piezoelectric device comprising a layer of a polymeric piezoelectric material disposed between a first and a second electrode; coupling mechanical stress derived from an environment to the piezoelectric device; and coupling electrical energy from the piezoelectric device.

BRIEF DESCRIPTION OF THE FIGURES

FIG. 9 is a block diagram of an electronic device powered by an inertial energy harvester using a piezoelectric bistable structures like those of FIG. 4.

FIG. 10 is a schematic diagram of an electronic device powered by a magnetically-triggered piezoelectric bistable structure.

FIG. 11 is a schematic sketch illustrating a pacemaker implanted in a human chest, with leads extending to the heart.

FIG. 12 illustrates a linear array of piezoelectric devices.

FIG. 13-15 illustrate an energy-harvesting sheathe surrounding a pacemaker lead, in an embodiment.

DETAILED DESCRIPTION OF THE EMBODIMENTS

A bistable structure is one that has a first and a second stable mechanical shape, particularly where they are stabilized by different curvature axes.

We have found that a piezoelectric material formed into a bistable mechanical structure, the bistable mechanical structure coupled to receive mechanical energy from an environment, can harvest energy from the environment more efficiently than a piezoelectric structure formed into other shapes. As forces are applied, sudden flexing from the first to second stable mechanical shape, or return from second to first stable shape provides a sudden, sharp, stress to the piezoelectric material that results in significant electrical power generation in the piezoelectric material.

Figure 1:
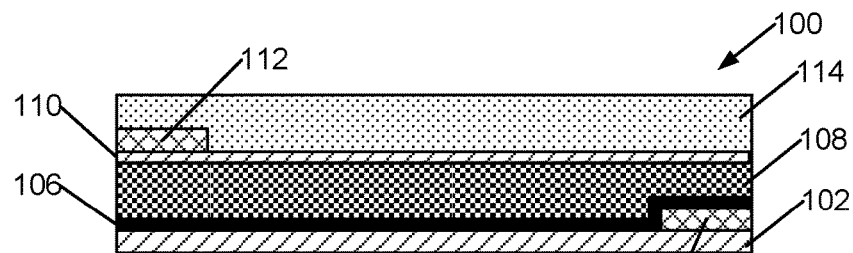
FIG. 1 is a cross sectional view of a polyvinylidene fluoride (PVDF) piezoelectric structure at high magnification.

FIG. 1 is a cross sectional view of a mesoporous polyvinylidene fluoride (PVDF) piezoelectric structure 100, polyvinylidene fluoride being a polymeric piezoelectric material. A supporting layer 102 is coated and masked with electrode interconnect 104, then a bottom electrically-conductive electrode layer 106 is applied. Bottom electrically-conductive electrode layer 106 and interconnect 104 are typically metallic. A mesoporous layer of polyvinylidene difluoride (PVDF) 108 is then formed atop the conductive electrode layer 106. Atop the PVDF layer is a top electrical contact layer 110 and an interconnect layer 112. An insulating plastic layer 114 is provided atop the entire structure, in biological applications the insulating layer is formed of a biocompatible plastic. Supporting layer 102 is chosen to be a moderately stiff material such as polyimide such as Kapton, or in an alternative embodiment polydimethylsiloxane (PMDS), PVDF copolymers have much smaller Young's modulus than piezoelectric ceramics or solid piezoelectric crystals like quartz, and have relatively high piezoelectric constants so that they generate significant electrical energy when mechanically stressed.

Figure 2:
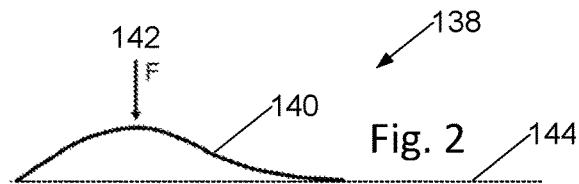
FIG. 2 is a cross sectional view at low magnification of a PVDF piezoelectric structure at low magnification and in a first state.
Figure 3:
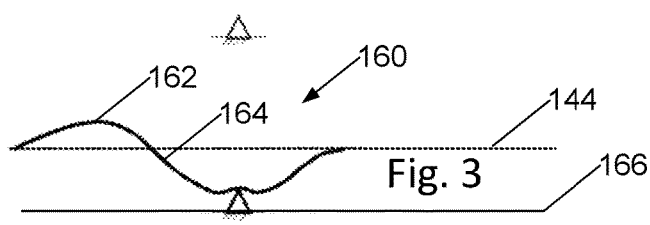
FIG. 3 is a cross sectional view at low magnification of a PVDF piezoelectric structure at low magnification and in a second state.

The layered PVDF piezoelectric structure 100 is formed in a partial loop 140 as illustrated in FIG. 2; this is its first state. When pressure is applied along a vector 142 perpendicular to a long axis 144 denoted by ends of the device 138, the partial loop 140 suddenly buckles at a point 164 to allow it to take on a second state 160 as illustrated in FIG. 3. With appropriate forces, structure 162 will return to the first state illustrated in FIG. 2. In some embodiments, partial loop 140 is formed over, and spaced from, a flat substructure 166 that serves to limit displacement from first to second state.

In an embodiment, the PVDF layered piezoelectric structure is formed as an array of loops 180 on a flat base 182, as illustrated in FIGS. 4, 5, 6, and 7.

Figure 22:
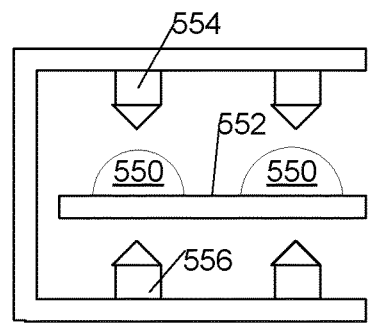
FIG. 22 illustrates an alternative embodiment of a bistable PVDF piezoelectric shape.
Figure 6:
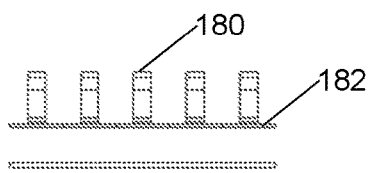
FIG. 6 is an end view of the array of PVDF piezoelectric bitable structures of FIG. 4.
Figure 7:
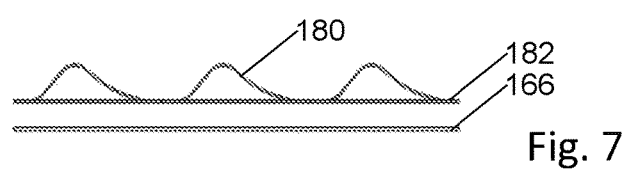
FIG. 7 is a lateral view of the array of PVDF piezoelectric bistable structures of FIG. 4.

In an alternative embodiment, the PVDF layered piezoelectric structure is formed as multiple bistable domes 550 (FIG. 22) on a flat base 552. The domes 552 may be coupled to the environment by stringing on a rod or through prods 554, 556 that couple environmental movements as mechanical stress to press on, and evert, the domes in a frequently reversible manner. For example, if flat base 552 is coupled to a moving weight, prod 554 may evert the dome as base 552 rises, and prod 556 may evert the dome 550 as base 552 falls.

Figure 4:
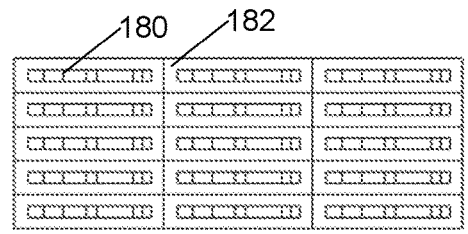
FIG. 4 is a top plan view of an array of PVDF piezoelectric bistable structures.
Figure 5:
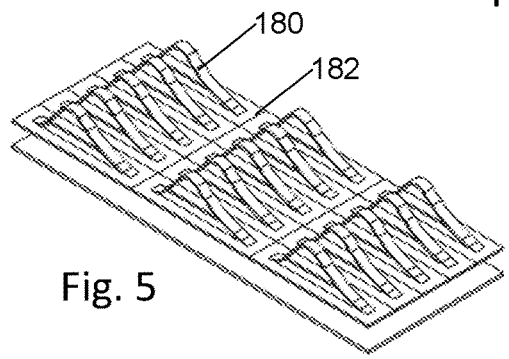
FIG. 5 is a perspective view of the array of PVDF piezoelectric bistable structures of FIG. 4.
Figure 8:
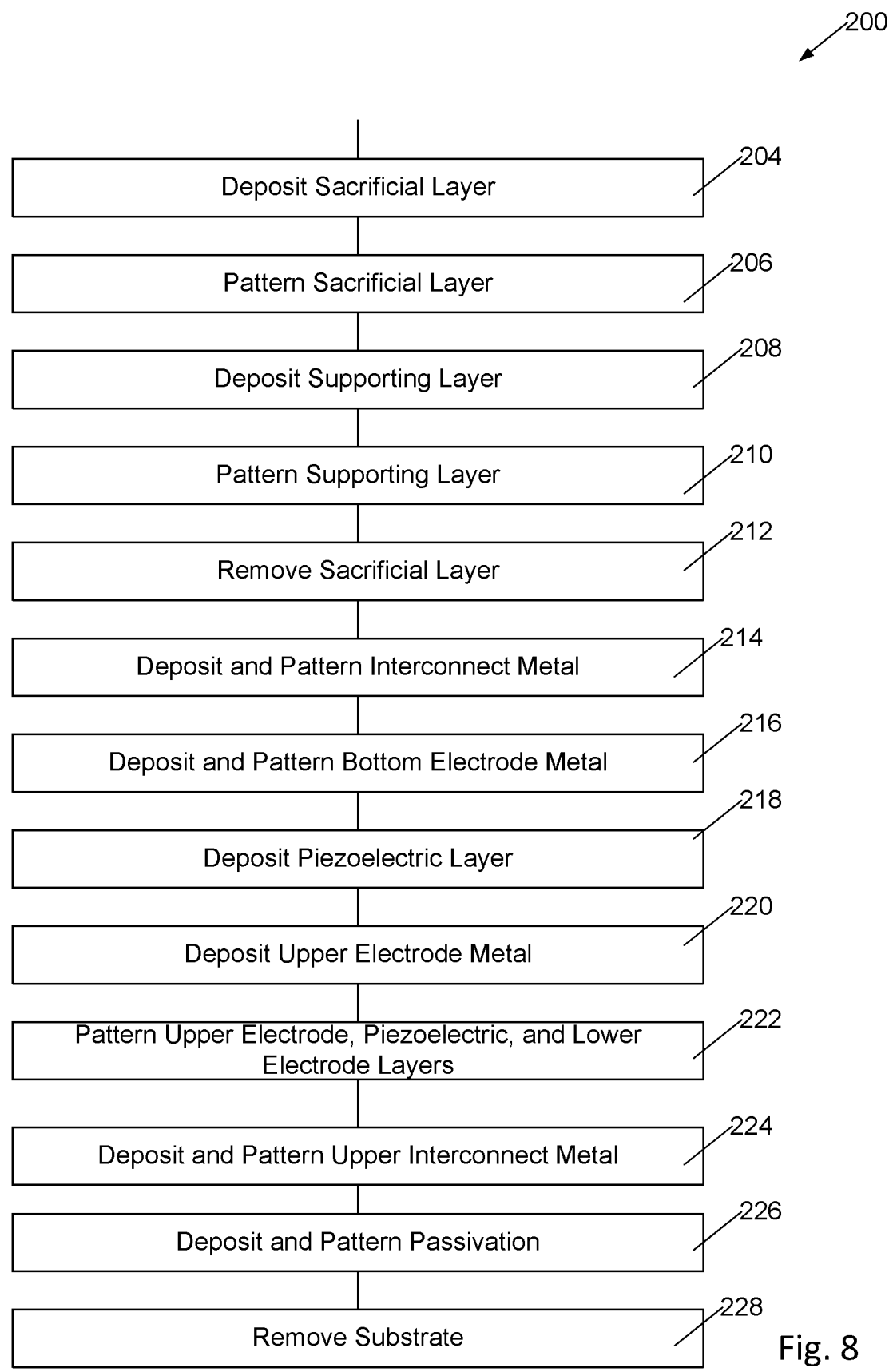
FIG. 8 is a flowchart of a method of manufacture of the array of PVDF piezoelectric bistable structures of FIG. 4.
Figure 23:
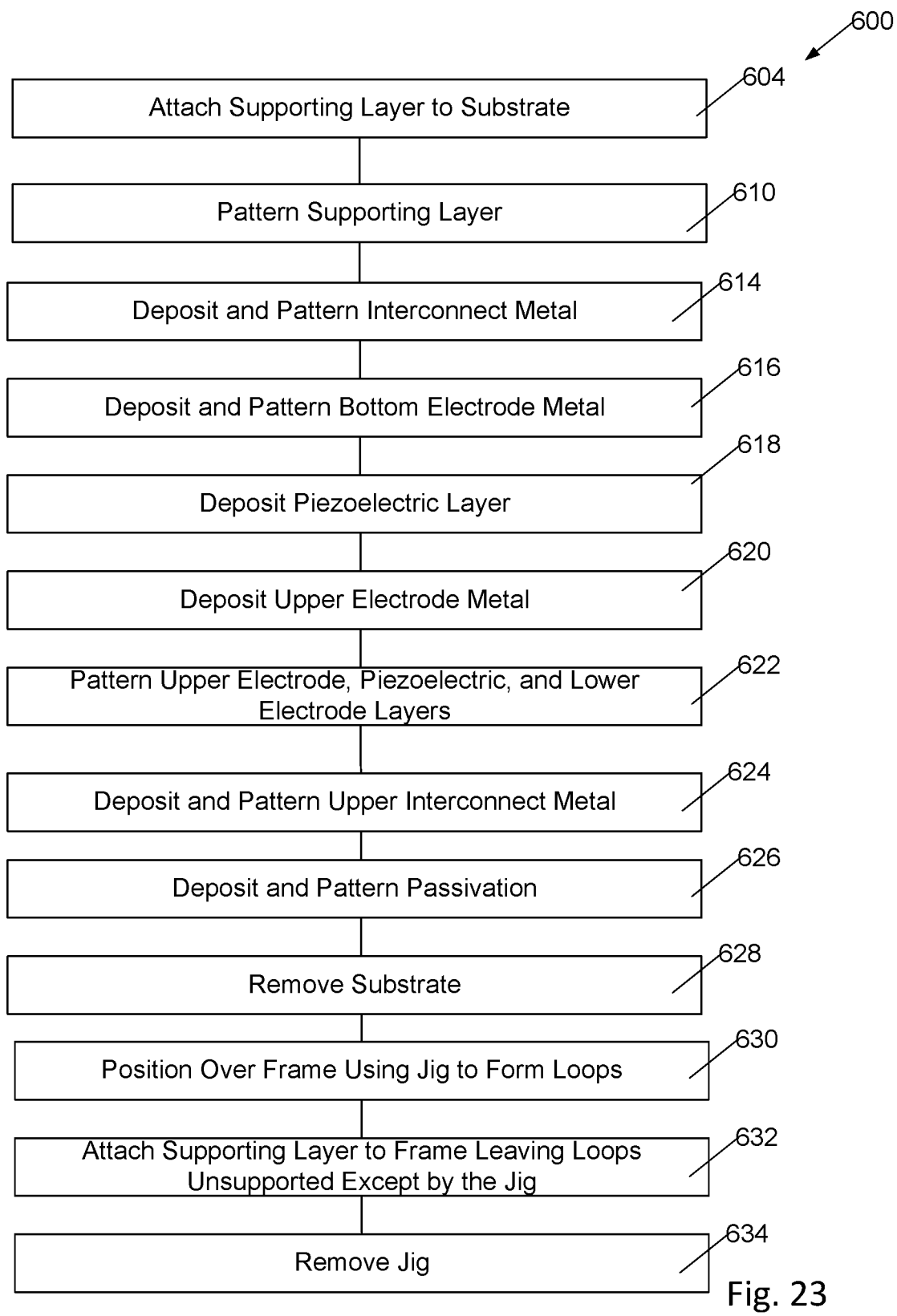
FIG. 23 is a flowchart illustrating an alternative method of manufacture of bistable PVDF piezoelectric shapes.

The structure of FIG. 4 is formed by a process 200 (FIG. 8); an alternative process is illustrated in FIG. 23 discussed below. A substrate is prepared and a sacrificial layer or layers is deposited 204 on the substrate. This sacrificial layer is patterned 206 to be present and high at points that will be high parts of loop 180, and absent at points where loop 180 of the piezoelectric structure is to be in contact with flat base 182. Next, supporting layer 102 (FIG. 1) is deposited 208 over both the substrate and sacrificial layer, masked, and etched to pattern 210 it. The sacrificial layer is then removed 212. The remaining supporting layer 102 has electrode interconnect deposited 214 upon it and masked to define electrode interconnect 104, then a bottom electrically-conductive electrode layer 106 is deposited 216. The piezoelectric layer 108, which in particular embodiments is PVDF and in other embodiments comprises other piezoelectric materials, is then deposited 218 atop the conductive electrode layer 106. Atop the PVDF layer is deposited 220, and top electrical contact layer 110 is deposited. The top and bottom electrode layers 106, 110 and piezoelectric 108 layers are then masked and patterned 222 if not done earlier. Then interconnect layer 112 is deposited and patterned 224. An insulating plastic layer 114 is deposited 226 atop the entire structure and patterned to disconnect a middle portion of loop 180 from adjacent base 182. Then, in some embodiments, the substrate is removed 228 to permit snap-through of the PVDF layered bistable structure.

In an alternative embodiment, the structure of FIG. 4 is formed by a process 600 (FIG. 23). A substrate is prepared and a sheet of polyimide that will serve as supporting layer 102 (FIG. 1) is attached 604 to the substrate. The supporting layer is masked and etched to define 610 what will become individual piezoelectric loops. The remaining supporting layer 102 has electrode interconnect deposited 614 upon it and masked to define electrode interconnect, then a bottom electrically-conductive electrode layer 106 is deposited 616. The piezoelectric layer 108, which in particular embodiments is PVDF and in other embodiments comprises other piezoelectric materials, is then deposited 618 atop the conductive electrode layer 106. Atop the PVDF layer is deposited 620, and top electrical contact layer 110 is deposited. The top and bottom electrode layers 106, 110 and piezoelectric 108 layers are then masked and patterned 622 if not done earlier. Then interconnect layer 112 is deposited and patterned 624. An insulating plastic layer 114 is deposited 626 atop the entire structure. Then, the substrate is removed 628 from the assembly of supporting layer, electrodes, interconnect, and piezoelectric layer. After the substrate is removed, a frame having first and second sides in fixed relationship to each other is positioned over a jig having a central protrusion; the assembly of supporting layer, electrodes, interconnect, and piezoelectric layer is draped over the central protrusion of the jig onto the first and second sides of the frame thereby forming 630 the assembly into loops. The supporting layer is thereupon firmly attached 632 to the first and second sides of the frame. The jig is then removed 634 to permit movement of the loops, including snapthrough. In the embodiments of FIGS. 4, 5, 6, 7, and 22, mechanical stress derived from the environment and applied to a top surface of the PVDF layered bistable structure may cause the bistable structure to change state thereby applying mechanical stress to the PVDF layer and generating a voltage.

In an embodiment of a device 250 (FIG. 9) powered by an energy harvester embodying the PVDF bistable structures of FIG. 4, a weight 252 is positioned between two arrays 254, 256 of the bistable structures, the arrays 254, 256 and weight 252 are positioned in a housing 258 such that as the device 250 is accelerated in an axis 260, the weight presses on one of the arrays, such as array 254, alternately with pressing on the other array 256. The top and bottom electrodes of the piezoelectric arrays 254, 256 are electrically coupled through the interconnect layers and in some embodiments lead wires to a power converter 262 that smooths pulsations of power from the arrays and regulates charging of one or both of a capacitor and battery 264. Battery 264 provides electrical power to electronics 266. Vibration and movement of device 250 generates power sufficient to maintain charge of battery 264 and operate electronics 266.

In another embodiment 300, FIG. 10, a piezoelectric bistable structure 302 is supported between clamps 304. A magnet 306 is attached to structure 302. Piezoelectric bistable structure 302 is coupled to a power converter 310, an energy storage device including a capacitor and/or battery 312, and electronics 314. A second magnet or magnets 316 is attached to moving objects, such as a flywheel 318 or a muscle, such that the magnet or magnets 316 passes near piezoelectric bistable structure 302 such that magnetic fields from magnet 316 applies mechanical stress through magnet 306 to piezoelectric bistable 302 by moving magnet 306 relative to clamps 304. In a particular embodiment, magnets 316 have alternating magnetic poles such that magnet 306 is alternately attracted to, and repelled by, magnets 316 as they move past magnet 306. As magnet 306 moves, piezoelectric bistable 302 is actuated from first to second state, or second to first state, generating pulses of electricity that are processed by power converter 310 to charge capacitor and/or battery 312 and power electronics 314.

A pacemaker 350 (FIG. 11), or pacemaker-internal defibrillator, implanted in a human chest 352, has leads 354 extending to the heart 356.

In an embodiment, an array of piezoelectric bistable devices of FIG. 4 is bonded to a surface of the pacemaker 350. The pacemaker is implanted deep in, or under, pectoral muscles of a subject, such that movement of the muscles causes a varying pressure on the pacemaker; the varying pressure applies mechanical stress to the bistable devices thereby causing the bistable devices to generate power that is harnessed to recharge a battery of the pacemaker.

In another embodiment, an array of bistable piezoelectric devices 400 (FIGS. 13, 14, and 15) are positioned around a pacemaker lead 402 within an outer sheathe 404, feeding through wires 406 to a power converter of pacemaker 350 or other implantable device. The energy harvesting sheathe illustrated in FIGS. 13-15 need not surround the entire length of lead 402, it is sufficient that it surround a portion of lead 402 implanted in an area that is subjected to frequent pressure changes and/or movements by muscular action-the muscular action may include heartbeats, in a particular embodiment the energy harvesting sheathe portion of lead 402 is positioned at a point 358 adjacent heart muscle near the apex of the heart.

Implantable energy harvesters, such as those of FIG. 9, 10, 11, or 14, using the bistable piezoelectric device of FIG. 4 are not limited to use with pacemakers. In alternative embodiments, the energy harvesters are used to harvest neck and jaw muscle movements to power deep brain stimulators such as are useful for treatment of Parkinson's disease, seizures, or chronic pain, to power electronic retina or cortical stimulation devices for providing limited vision to the blind, or to power other implantable electronic devices.

Kirigami is an art of paper folding, similar to origami except cuts are permitted. Kirigami-based piezoelectric structures 450, 460 (FIGS. 16-18) are formed of the piezoelectric PVDF structure of FIG. 1 formed as a sheet 452, 454 in the embodiments of FIGS. 16-18 the sheet 452, 454 is curved. In a first Kirigami embodiment 450 (FIGS. 16-17) notches 456 are cut in both sides of sheet 452 in pairs, alternating with central slots 458. In a second Kirigami embodiment 460 (FIG. 18), notches 462, 464 are cut in alternating sides of sheet 454. In both embodiments, interconnect 104, 112 (FIG. 1) are brought out through leads 470 coupled to power converter electronics. In both Kirigami embodiments, application of tension along the long axis of sheet 452, 454 causes the sheet to twist as shown in FIG. 19 where the flat sheet 454 of FIG. 18 has become a longer sheet 466 with openings 468 forming as notches 463, 464 pull apart.

Figure 16:
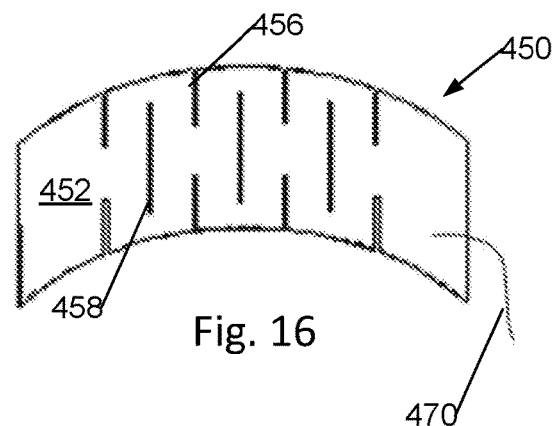
FIGS. 16-19 illustrate alternative embodiments wherein Kirigami-based energy harvesters use the PVDF structure of FIG. 1.
Figure 17:
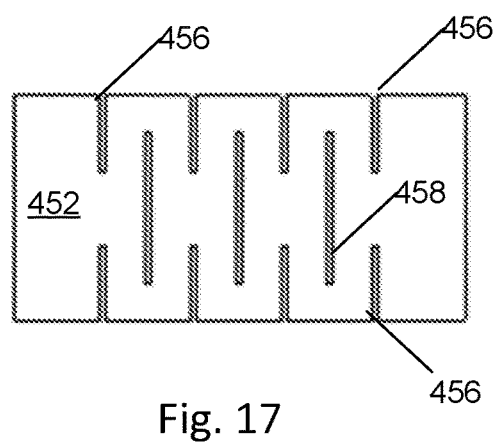
Figure 19:
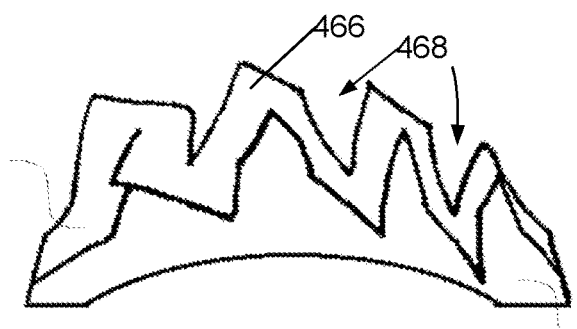
Figure 18:
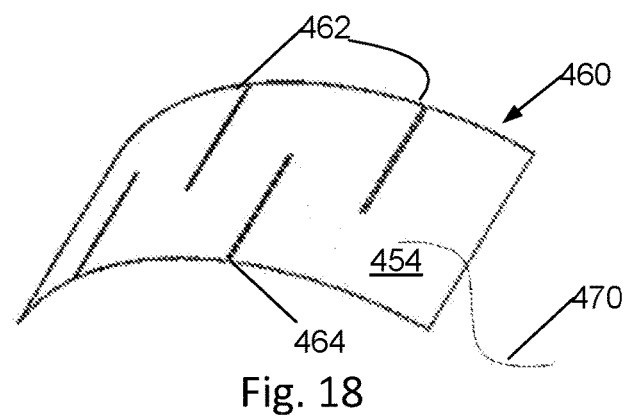

Twisting of the PVDF structure of FIG. 1 in the embodiments of FIGS. 16-19 results in generation of electrical power through the piezoelectric effect as the devices are alternately stretched into the elongated form of FIG. 19 and the more relaxed form of FIG. 16-18 by mechanical stress received from the environment. This effect is used in a first embodiment of an energy harvester by affixing each end of the piezoelectric sheet to an end of a surrounding elastomeric tube, and anchoring ends of the elastomeric tube, in parallel with a muscle, to two different bones of an organism, the bones being coupled by a synovial joint and subjected to relative motion. Wires 470 from interconnect layers 104, 112 are brought out of the tube to the electronics to be powered.

In an alternative embodiment 500 (FIG. 20), a weight 502 confined in a box 504 is attached to one end of the Kirigami structure 506 of FIGS. 16-19, the other end 508 of structure 506 being anchored to another end of box 504. Structure 506 may pass through a hole in a partition 510, the partition intended to limit movement of weight 502. Weight 502 flops back and forth as box 504 tilts or is accelerated thereby alternating the Kirigami structure 506 between the extended state shown in FIG. 20 and the compressed state 506A shown in FIG. 21.

Figure 20:
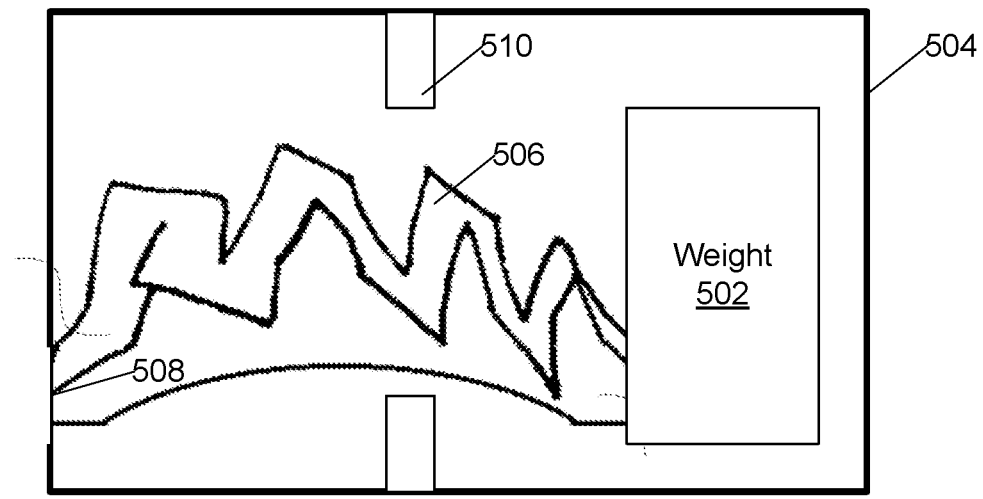
FIGS. 20-21 illustrate an embodiment of an energy harvester using the Kirigami-based piezoelectric structures of FIGS. 16-19.
Figure 21:
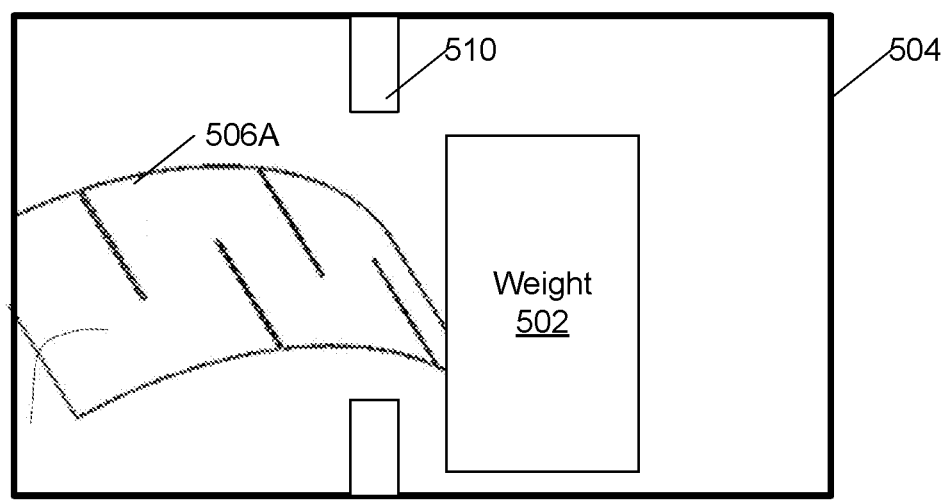

A weight-actuated energy harvester 500 such as that of FIG. 20-21 or 250 of FIG. 9 may be implanted into a mammal, including a human, attached to a backpack to recharge a cell phone while the backpack is being worn, installed within a pedometer to power the pedometer, or attached to a backhoe arm or pumpjack arm to power telemetry devices, where it is subject to repeated movements sufficient to shift the weight relative to the remainder of the energy harvester to harvest energy from the environment to power associated small, low-power, electronic devices.

Combinations of Features

The various features described herein may be combined in various combinations. Among combinations anticipated include:

A piezoelectric energy harvester designated A including a layered structure comprising a first electrode, a polymeric piezoelectric material, and a second electrode, the layered structure coupled to receive mechanical stress from the environment, and the first and second electrode electrically coupled to a power converter. The power converter is adapted to charge an energy storage device selected from a capacitor and a battery.

An energy harvester designated AA including the energy harvester designated A wherein the polymeric piezoelectric material comprises polyvinylidene fluoride (PVDF).

An energy harvester designated AB including the energy harvester designated A wherein the energy harvester is coupled to provide power to an implantable device selected from the group consisting of a pacemaker and a deep brain stimulator.

An energy harvester designated AC including the energy harvester designated A wherein the energy harvester is coupled to provide power to a device selected from a telemetry device, a pedometer, and a cellphone.

An energy harvester designated AD including the energy harvester designated A, AA, AB, or AC wherein the mechanical stress is derived from movement of the energy harvester through a weight within the energy harvester.

An energy harvester designated AE including the energy harvester designated A, AA, AB, AC, or AD wherein the layered structure is formed as multiple partial loops, the mechanical stress coupled to a top of the partial loops.

An energy harvester designated AF including the energy harvester designated AE wherein the multiple partial loops each form a bistable structure.

An energy harvester designated AG including the energy harvester designated A, AA, AB, AC, or AD wherein the layered structure is formed as domes on a surface, the mechanical stress coupled to the domes, the domes forming a bistable structure.

An energy harvester designated AH including the energy harvester designated A, AA, AB, AC, or AD wherein the layered structure is formed as a sheet with multiple slots, the slots arranged to permit mechanical stress to stretch the structure by twisting the sheet.

A method of harvesting energy designated B from the environment comprising providing a piezoelectric device comprising a layer of a polymeric piezoelectric material disposed between a first and a second electrode; coupling mechanical stress derived from an environment to the piezoelectric device; and coupling electrical energy from the piezoelectric device.

A method of harvesting energy designated BA comprising the method designated B wherein the polymeric piezoelectric material comprises polyvinylidene fluoride (PVDF).

A method of harvesting energy designated BB comprising the method designated B or BA further comprising coupling the electrical energy to provide power to an implantable device selected from the group consisting of a pacemaker and a deep brain stimulator.

A method of harvesting energy designated BC comprising the method designated B, BA, or BB further comprising coupling the electrical energy to provide power to a device selected from a telemetry device, a pedometer, and a cellphone.

A method of harvesting energy designated BD comprising the method designated B, BA, BB, or BC wherein the mechanical stress is derived from movement and a weight.

A method of harvesting energy designated BE comprising the method designated B, BA, BB, BC, or BD wherein the layered structure is formed as multiple partial loops, the mechanical stress coupled to a top of the partial loops.

A method of harvesting energy designated BF comprising the method designated BE wherein the multiple partial loops each form a bistable structure.

A method of harvesting energy designated BG comprising the method designated B, BA, BB, BC, or BD wherein the layered structure is formed as domes on a surface, the mechanical stress coupled to the domes, the domes forming a bistable structure.

A method of harvesting energy designated BH comprising the method designated B, BA, BB, BC, or BD wherein the layered structure is formed as a sheet with multiple slots, the slots arranged to permit mechanical stress to stretch the structure by twisting the sheet.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A piezoelectric energy harvester comprising:
a layered structure comprising a first electrode, a polymeric piezoelectric material, and a second electrode;
the layered structure coupled to receive mechanical stress from an environment;
the first and second electrode electrically coupled to a power converter;
the power converter adapted to charge an energy storage device selected from a capacitor and a battery;
wherein the layered structure is formed as multiple partial loops, wherein a plurality of the multiple partial loops are formed around a core structure.

2. The energy harvester of claim 1 further comprising a sheathe around the multiple partial loops formed around the core structure.

3. The energy harvester of claim 2 wherein the core structure is a lead.

4. The energy harvester of claim 3 wherein the energy harvester is implanted to harvest energy from neck and jaw muscle movements and is coupled to power a deep-brain stimulator.

5. The energy harvester of claim 3 wherein the energy harvester is implanted to harvest energy from movements of pectoral muscles and is coupled to power a pacemaker.

6. The energy harvester of claim 1 wherein the energy harvester is implanted to harvest energy from neck and jaw muscle movements and is coupled to power a deep-brain stimulator.

7. The energy harvester of claim 1 wherein the energy harvester is implanted to harvest energy from movements of pectoral muscles and is coupled to power a pacemaker.

8. The energy harvester of claim 3, wherein the lead is a lead of an implantable device.

9. The energy harvester of claim 8, wherein:
the implantable device comprises the power converter and the energy storage device; and
the power converter is adapted to charge the energy storage device with electrical energy from the layered structure.

10. The energy harvester of claim 9, wherein the implantable device comprises a pacemaker.

11. A piezoelectric energy harvester comprising:
a layered structure comprising a first electrode, a polymeric piezoelectric material, and a second electrode;
the layered structure coupled to receive mechanical stress from an environment;
the first and second electrode electrically coupled to a power converter;
the power converter adapted to charge an energy storage device selected from a capacitor and a battery;
wherein the layered structure is formed as multiple partial loops, wherein a plurality of the multiple partial loops are formed around a lead of an implantable device.

12. The energy harvester of claim 11 further comprising a sheathe around the multiple partial loops formed around the core structure.

13. The energy harvester of claim 12 wherein the energy harvester is implanted to harvest energy from neck and jaw muscle movements and is coupled to power a deep-brain stimulator.

14. The energy harvester of claim 12 wherein the energy harvester is implanted to harvest energy from movements of pectoral muscles and is coupled to power a pacemaker.

15. The energy harvester of claim 14, wherein: the implantable device comprises the power converter and the energy storage device; and the power converter is adapted to charge the energy storage device with electrical energy from the layered structure.

* * * * *